United States Patent
Kobayashi et al.

(10) Patent No.: US 8,251,510 B2
(45) Date of Patent: Aug. 28, 2012

(54) OPHTHALMIC OBSERVATION APPARATUS AND OPHTHALMIC OBSERVATION PROGRAM

(75) Inventors: Masahiko Kobayashi, Aichi-ken (JP); Yoshiyuki Yamada, Toyokawa (JP)

(73) Assignee: Nidek Co., Ltd, Gamagori-shi, Aichi-Ken (JP)

( * ) Notice: Subject to any disclaimer, the term of this patent is extended or adjusted under 35 U.S.C. 154(b) by 115 days.

(21) Appl. No.: 12/729,703

(22) Filed: Mar. 23, 2010

(65) Prior Publication Data

US 2010/0238403 A1   Sep. 23, 2010

(30) Foreign Application Priority Data

Mar. 23, 2009  (JP) ................................. 2009-070797
Mar. 23, 2009  (JP) ................................. 2009-070798

(51) Int. Cl.
*A61B 3/14* (2006.01)
(52) U.S. Cl. ...................................................... 351/206
(58) Field of Classification Search .................. 351/205, 351/206, 210, 221, 246
See application file for complete search history.

(56) References Cited

U.S. PATENT DOCUMENTS

| | | | |
|---|---|---|---|
| 6,086,205 A | 7/2000 | Svetliza | |
| 7,510,282 B2 | 3/2009 | Ueno et al. | |
| 7,768,652 B2 * | 8/2010 | Everett | 356/497 |
| 7,784,942 B2 * | 8/2010 | Maeda et al. | 351/206 |
| 2003/0016782 A1 | 1/2003 | Kaufman et al. | |
| 2003/0185426 A1 | 10/2003 | Ohishi | |
| 2004/0100503 A1 | 5/2004 | Morita et al. | |
| 2005/0094099 A1 | 5/2005 | Newman et al. | |
| 2006/0025658 A1 | 2/2006 | Newman et al. | |
| 2008/0084538 A1 | 4/2008 | Maeda et al. | |
| 2010/0014050 A1 | 1/2010 | Newman et al. | |
| 2010/0238404 A1 | 9/2010 | Newman et al. | |
| 2010/0238405 A1 | 9/2010 | Newman et al. | |

FOREIGN PATENT DOCUMENTS

| | | |
|---|---|---|
| EP | 1336376 A1 | 8/2003 |
| EP | 1527731 A1 | 5/2005 |
| EP | 1908397 A2 | 4/2008 |

* cited by examiner

*Primary Examiner* — Huy K Mai
(74) *Attorney, Agent, or Firm* — Muncy, Geissler, Olds & Lowe, PLLC (57) ABSTRACT

An ophthalmic observation apparatus that is capable of performing follow-up of an examinee's eye efficiently and suitably. The ophthalmic observation apparatus for observing an image of an examinee's eye that is obtained by an ophthalmic photographing apparatus includes an input device arranged to output an operation signal given by an examiner, a monitor, and a display control unit arranged to display a first image and a second image of a same portion of the examinee's eye that are obtained at different dates and times of examination on the monitor in a comparable manner, and when changing a display region of the image of the examinee's eye based on the operation signal outputted from the input device, synchronize the change of the display region between the first image and the second image.

9 Claims, 6 Drawing Sheets

FIG. 9

OPHTHALMIC OBSERVATION APPARATUS AND OPHTHALMIC OBSERVATION PROGRAM

BACKGROUND OF THE INVENTION

1. Field of the Invention

The present invention relates to an ophthalmic observation apparatus arranged to observe an image of a given portion of an examinee's eye that is photographed by an ophthalmic photographing apparatus, and an ophthalmic observation program.

2. Description of Related Art

In an ophthalmic photographing apparatus such as an ophthalmic optical coherence tomography (OCT) apparatus, a fundus camera, and a scanning laser ophthalmoscope (SLO), images of one portion of an examinee's eye are obtained at different dates and times of examination in order to perform follow-up on the portion of the examinee's eye. In the case of the ophthalmic OCT apparatus, a tomographic image of a fundus is obtained a plurality of times, and follow-up is performed on a diseased portion of the examinee's eye based on the change of the tomographic images.

In such a case, data on an appropriate eye image is selected among eye images stored in an ophthalmic image filing system, and follow-up is performed based on the eye image displayed on a screen of a display monitor.

Citation List

Patent Literature

Patent literature 1: Japanese Patent Application Laid-open Publication No. 2008-29467

However, in the conventional configuration, only the selected eye image is displayed on the monitor, which is not enough in visually comparing the images in the same portion of the examinee's eye.

SUMMARY OF THE INVENTION

An object of the invention is to overcome the problems described above and to provide an ophthalmic observation apparatus that is capable of performing follow-up of an examinee's eye efficiently and suitably, and an ophthalmic observation program.

To achieve the objects and in accordance with the purpose of the present invention, an ophthalmic observation apparatus for observing an image of an examinee's eye that is obtained by an ophthalmic photographing apparatus includes an input device arranged to output an operation signal given by an examiner, a monitor, and a display control unit arranged to display a first image and a second image of a same portion of the examinee's eye that are obtained at different dates and times of examination on the monitor in a comparable manner, and when changing a display region of the image of the examinee's eye based on the operation signal outputted from the input device, synchronize the change of the display region between the first image and the second image.

In another aspect of the present invention, an ophthalmic observation program to be stored in a medium that is readable in a computer for observing an image of an examinee's eye that is obtained by an ophthalmic photographing apparatus effects an operation of the computer as a display control unit to display a first image and a second image of a same portion of the examinee's eye that are obtained at different dates and times of examination on the monitor in a comparable manner, and when changing a display region of the image of the examinee's eye based on an operation signal outputted from an input device, synchronize the change of the display region between the first image and the second image.

Additional objects and advantages of the invention are set forth in the description which follows, are obvious from the description, or may be learned by practicing the invention. The objects and advantages of the invention may be realized and attained by the ophthalmic observation apparatus and the ophthalmic observation program in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
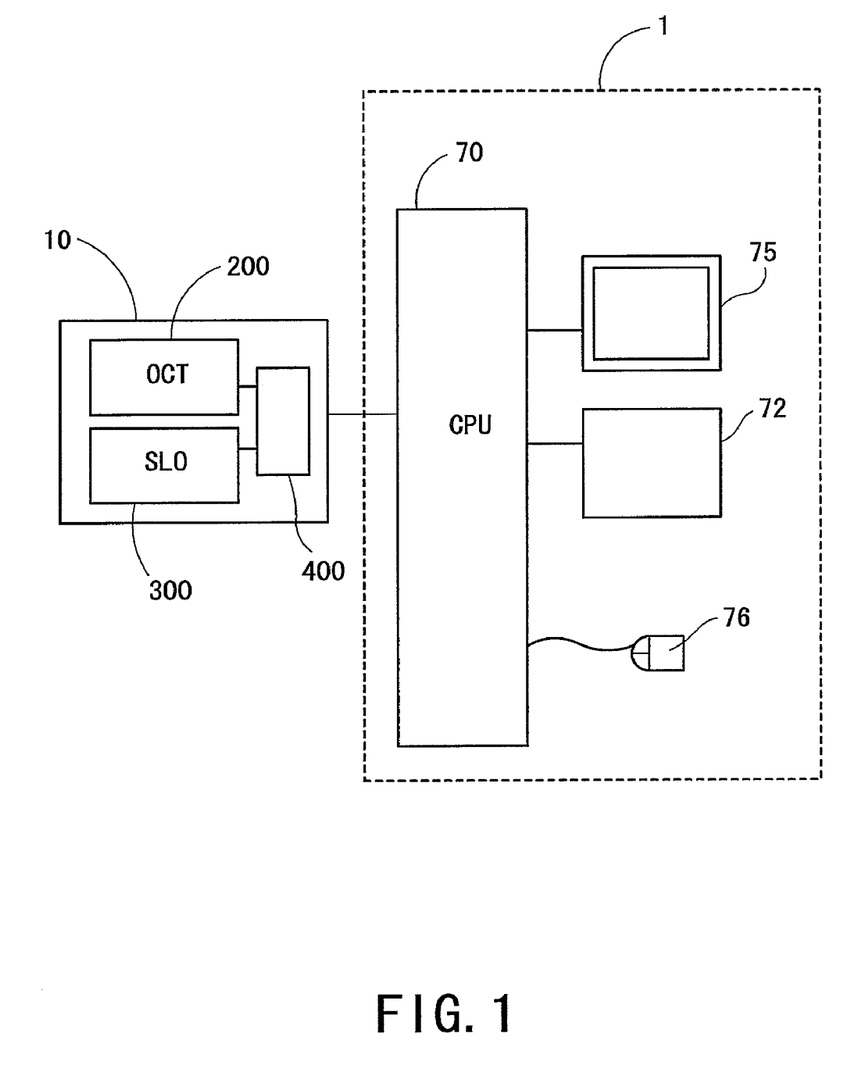
FIG. 1 is a block diagram for illustrating a configuration of an ophthalmic observation apparatus according to a preferred embodiment of the present invention.

A detailed description of one preferred embodiment of an ophthalmic observation apparatus and an ophthalmic observation program embodied by the present invention is provided below with reference to the accompanying drawings. FIG. 1 is a block diagram for illustrating a configuration of an ophthalmic observation apparatus according to the preferred embodiment of the present invention.

An ophthalmic observation apparatus 1 is arranged to observe a fundus image that is photographed by an ophthalmic photographing apparatus 10 on a monitor. The ophthalmic observation apparatus 1 includes a CPU (a calculation control unit) 70, a mouse (an operation input unit) 76, a memory (a storing unit) 72, and a monitor 75, and the units are electrically connected to the CPU 70 through a bus or other mechanisms.

The CPU 70 controls operations of the units based on an ophthalmic observation program and various control programs that are stored in the memory 72. Execution of the programs on the computer effects the operation of the ophthalmic observation apparatus 1. The CPU 70 controls a display screen of the monitor 75 following the ophthalmic observation program.

The mouse 76 includes a sensor arranged to detect a movement signal that is generated when the main body of the mouse 76 is two-dimensionally moved, two right and left mouse buttons depression of which are detected, and a wheel mechanism that is disposed between the two mouse buttons and is rotatable in a back and forth direction. For the CPU 70, the mouse 76, the memory 72, and the monitor 75, a calculation processing unit, an input unit, a storing unit, and a display unit of a commercially available PC (personal computer) in which the ophthalmic observation program is installed may be used.

The ophthalmic observation apparatus 1 is connected with the ophthalmic photographing apparatus 10 arranged to photograph an image of a given portion of an examinee's eye. As shown in FIG. 1, the ophthalmic photographing apparatus 10 includes an interference optical system (an OCT optical system) 200 arranged to obtain a tomographic image of the fundus, a front observation optical system 300 arranged to obtain a front image of the fundus, and a control unit 400, and thus is capable of photographing a fundus portion. For details of the configuration of the ophthalmic photographing apparatus 10, please refer to Japanese Patent Application Laid-Open No. 2008-

The interference optical system 200 includes a first light source, a first scanning unit (an optical scanner) arranged to scan first measurement light emitted from the first light source on the fundus, and a first photodetector arranged to photo-receive interference light that is obtained by synthesizing reference light formed of light emitted from the first light source and reflection light formed of the first measurement light projected onto the fundus. The interference optical system 200 accordingly has a configuration of a so-called ophthalmic optical coherence tomography (OCT) apparatus. The configuration of the interference optical system 200 may be Spectral-domain OCT (SD-OCT) using a spectrometer, Swept-source OCT (SS-OCT) using a wavelength variable light source, or Time-domain OCT (TD-OCT).

The front observation optical system 300 includes a second light source, a second scanning unit (an optical scanner) arranged to two-dimensionally scan second measurement light emitted from the second light source on the fundus, a second photodetector arranged to photo-receive the light reflected from the fundus through a confocal aperture disposed at a substantially conjugate position with the fundus. The front observation optical system 300 accordingly has a configuration of a so-called ophthalmic scanning laser ophthalmoscope (SLO). The configuration of the front observation optical system 300 may be a configuration of a fundus camera.

The control unit 400 controls the constituent members of the ophthalmic photographing apparatus 10 in order to obtain a tomographic image (an OCT image) based on a photo-receiving signal outputted from the first photodetector of the interference optical system 200, and a front image (an SLO image) based on a photo-receiving signal outputted from the second photodetector of the front observation optical system 300.

The ophthalmic observation apparatus 1 and the ophthalmic photographing apparatus 10 are connected to each other on a LAN or other mechanisms, and various pieces of data obtained by the ophthalmic photographing apparatus (e.g., tomographic image data, front image data, various photographing conditions at the time of image obtainment (e.g., a scanning position of the measurement light, the date and time of examination)) are transferred to the memory 72 as a data base.

Figure 2:
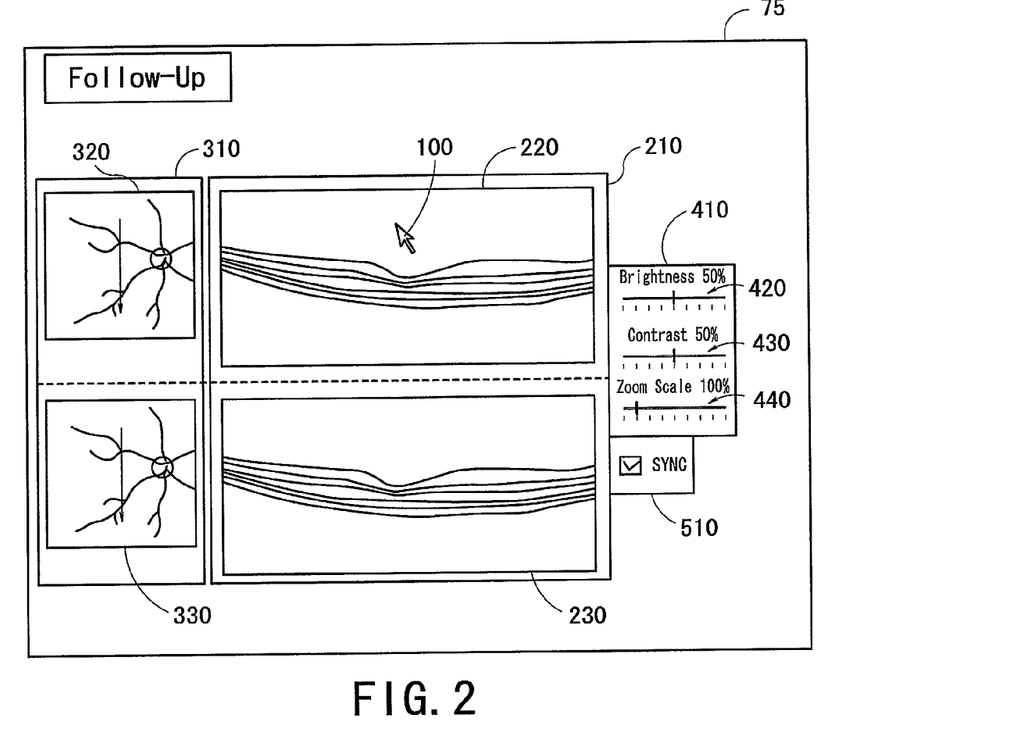
FIG. 2 shows an example of a display screen (a follow-up screen) displayed on a monitor.

FIG. 2 shows an example of the display screen (a follow-up screen) displayed on the monitor 75. The screen of the monitor 75 includes a cursor 100 that is movable all over the screen of the monitor 75 by moving operation of the mouse 76, a tomographic image display region 210, a front image display region 310, a display condition setting region 410 for adjusting display conditions of tomographic images displayed on the tomographic image display region 210, and a synchronizing button 510 for selecting whether or not to synchronize change of the display condition/the display region between the tomographic images that are obtained at different dates and times of examination.

The CPU 70 moves the cursor 100 on the screen of the monitor 75 based on an operation signal that is outputted from the mouse 76 when the mouse 76 is operated by an examiner. When a click operation or a drag operation is performed with the cursor 100 placed at an intended position on the monitor 75, the display condition/the display region are set. The cursor 100 is used for designating an arbitrary position on the monitor 75.

On the tomographic image display region 210, a first tomographic image 220 and a second tomographic image 230 that are obtained at different dates and times of examination and stored in the memory 72 are displayed on their given display areas in a comparable manner. In this case, the tomographic image 220 and the tomographic image 230 that are displayed are at least portions of the tomographic image data stored in the memory 72. In FIG. 2, tomographic images of a macular spot are displayed as tomographic images in the same portion.

The CPU 70 refers to the information on the date and time of examination of each of the image data provided to each of the image data (not shown) and displays an image that is obtained at an earlier date and time of examination on the upper portion of the monitor 75 and an image that is obtained at a later date and time of examination on the lower portion of the monitor 75.

At the time of displaying the tomographic image 220 and the tomographic image 230 on the monitor 75, the examiner previously selects, on a given image selecting screen (not shown), arbitrary tomographic images that are obtained at different dates and times of examination from the image data of the same portion (e.g., a macular spot portion of a fundus) of the same examinee stored in the memory 75 and calls up the follow-up screen. By this operation, two selected images that are obtained at different dates and times of examination are displayed on one screen. Photographed portions of the tomographic images are specified based on information on the scanning position of the measurement light, information on a fixation position, and other information that are stored in the memory 72 simultaneously with the image obtainment.

On the front image display region 310, front images that are obtained substantially simultaneously with the tomographic images displayed on the tomographic image display region 210 and stored in the memory 72 are displayed on their given display areas in a comparable manner. A first front image 320 corresponds to the first tomographic image 220, and a second front image 330 corresponds to the second tomographic image 230. The first front image 320 and the second front image 330 are outputted to the monitor 75 upon selecting the tomographic images.

On the display condition setting region 410, a brightness adjusting section 420 arranged to adjust the brightness of the tomographic images, a contrast adjusting section 430 arranged to adjust the contrast of the tomographic images, and a zoom scale adjusting section 440 arranged to adjust the zoom scale (display scale) of the tomographic images are displayed. Initial settings are configured such that the brightness is 50%, the contrast is 50%, and the zoom scale is 100%. When display positions of sliders of the adjusting units are changed by operation of the mouse 76, the CPU 70 changes the display conditions of the tomographic images.

At the time of the rotating operation of the wheel mechanism of the mouse 76 with the cursor 100 pointing the tomographic image 220 or the tomographic image 230, the CPU 70 changes the zoom scale of the tomographic image based on an operation signal outputted from the mouse 76. At the time of the drag operation of the mouse 76 with the cursor 100 pointing the tomographic image 220 or the tomographic image 230, the CPU 70 changes a region of the tomographic image to be displayed on the monitor (the display region) based on the operation signal outputted from the mouse 76.

Figure 3:
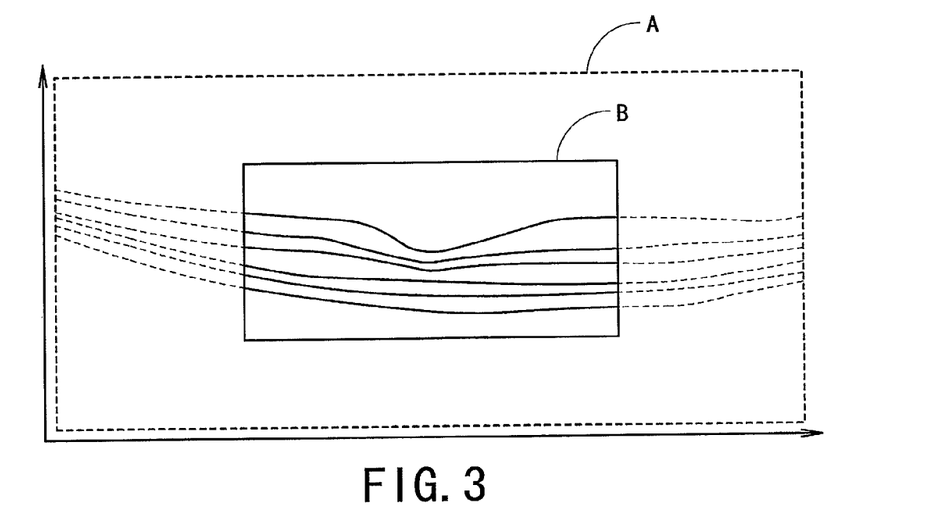
FIG. 3 is a schematic view for illustrating change of a display scale and a display region of a tomographic image displayed on the monitor.

FIG. 3 is a schematic view for illustrating the change of the display scale and the display region of the tomographic image displayed on the monitor 75. The rectangular region shown by dashed lines represents tomographic image data A stored in the memory 72. The image data A is zoomed in or out according to the zoom scale. The rectangular region shown by solid lines represents a region B in the image data A that is actually displayed on the monitor 75 (the display region). The display region B corresponds to the given display areas that are set for the tomographic images in the tomographic image display region 210. A region in the image data A that is enclosed by the display region B is displayed as the tomographic image 220 or the tomographic image 230 on the monitor 75.

At the time of output of the operation signal to instruct the change of the zoom scale, the CPU 70 changes the scale of the image data A with respect to the display region B (FIG. 3 shows the image data A when the zoom scale is 200%). Thus, the zoom scale of the tomographic image displayed on the monitor 75 is changed.

At the time of output of the operation signal to instruct the change of the display region, the CPU 70 moves the display region B in the up and down direction and the right and left direction with respect to the image data A at a given scale. Accordingly, the display region of the tomographic image displayed on the monitor 75 is changed. To be more specific, the CPU 70 continually detects a vector quantity (ΔX, ΔY) that has a starting point at a point where the drag operation of the mouse 76 starts and an endpoint at a point where the drag operation ends. The CPU 70 moves the display region B according to the detected vector quantity. The CPU 70 outputs tomographic image data corresponding to the moved display region B in the given area on the monitor 75. Thus, the tomographic image on the monitor 75 is scrolled in the up and down direction and in the right and left direction. This operation allows the examiner to easily observe an intended fundus portion in the tomographic image.

If the zoom scale is greater than 100%, the change of the display region of the tomographic image changes the fundus portion displayed on the monitor 75 in the depth direction and/or the right and left direction. If the zoom scale is equal to or smaller than 100%, the change of the display region of the tomographic image moves the fundus portion displayed on the monitor 75 in the depth direction and/or the right and left direction.

The method of changing the display region is not limited to the drag operation described above and may be any method of controlling display on the monitor 75 based on an operation signal concerning the up and down direction and the right and left direction. For example, the change of the display region may be performed by moving a scroll bar displayed on the monitor 75. In addition, the pointing device for outputting the operation signal concerning the up and down direction and the right and left direction is not limited to the mouse 76 and may be a track ball, a cross key of a key board, a touch panel, and other devices.

The synchronizing button 510 is used as a mode switching unit arranged to selectively switch the mode of the displaying between a synchronizing mode of synchronizing the change of the display condition/the display region of one of the two tomographic images and the change of the display condition/the display region of the other tomographic image, and a non-synchronizing mode of not synchronizing them. In the case of FIG. 2, checking the checkbox of the synchronizing button 510 places the apparatus into the synchronizing mode, and unchecking the checkbox of the synchronizing button 510 places the apparatus into the non-synchronizing mode.

A description of follow-up by the examiner by using the display screen for follow-up described above will be provided. When two tomographic images for follow-up are selected and displayed on the monitor 75, the examiner is allowed to observe the tomographic image 220 and the tomographic image 230. In the present preferred embodiment of the present invention, the preset mode is the synchronizing mode.

In the synchronizing mode, when the change of the display condition/the display region of one of the two tomographic images is performed, the CPU 70 performs the change of the display condition/the display region of the other tomographic image in synchronization with the change of the one of the tomographic images.

Figure 4:
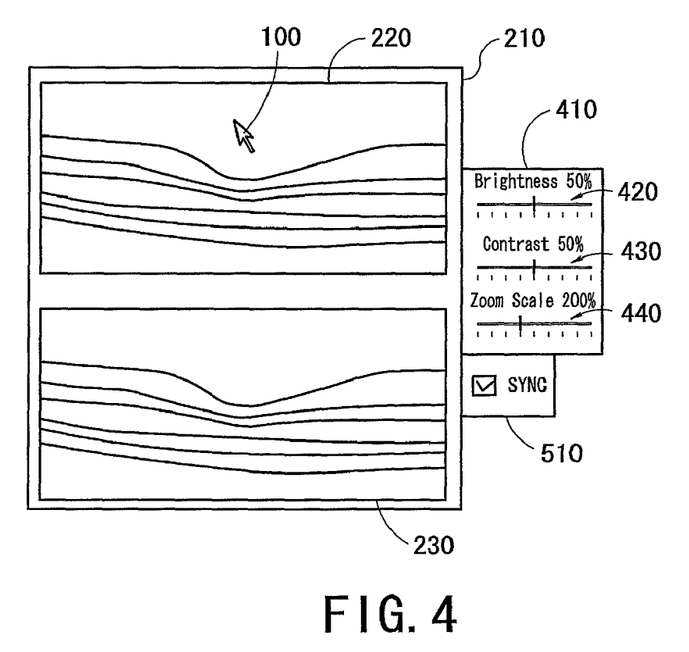
FIG. 4 shows an example of synchronizing the change of the display scale between two tomographic images that are obtained at different dates and times of examination.

To be more specific, in the case of changing the display scale in the synchronizing mode, the CPU 70 displays the tomographic image 220 and the tomographic image 230 at the same zoom scales in accordance with the zoom scale that is set by operating the slider of the zoom scale adjusting unit 440 or by the rotating operation of the wheel mechanism (see FIG. 4). By changing the zoom scale, the zoom scale of the tomographic image 220 and the zoom scale of the tomographic image 230 are changed synchronously. In a case where the apparatus is in the non-synchronizing mode and the zoom scale of the tomographic image 220 and the zoom scale of the tomographic image 230 are not equal, if the apparatus is placed into the synchronizing mode, the zoom scale of one of the tomographic images is adjusted to the zoom scale of the other tomographic image.

Also in the adjustment of the brightness and the contrast of the tomographic images, the CPU 70 displays the tomographic image 220 and the tomographic image 230 at the same brightnesses or the same contrasts by operating the slider of the brightness adjusting unit 420 or the contrast adjusting unit 430 in a similar manner to the adjustment of the zoom scale.

Figure 5:
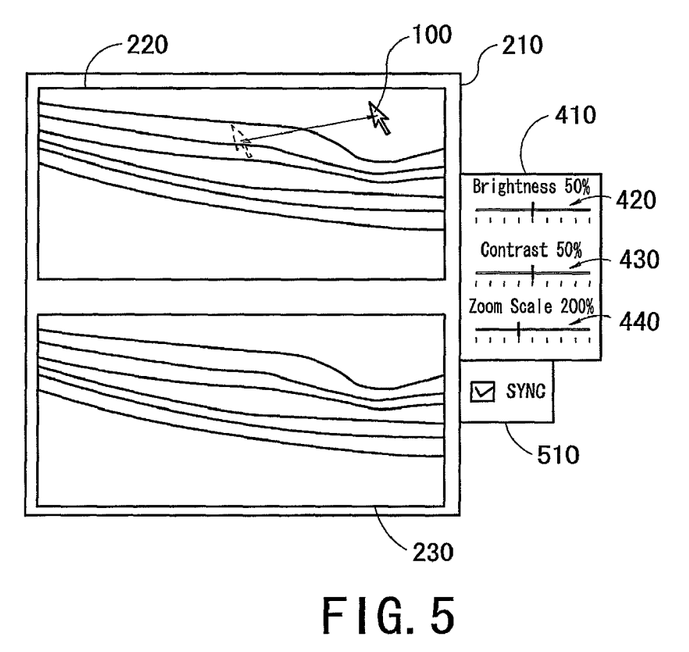
FIG. 5 shows an example of synchronizing the change of the display region between two tomographic images that are obtained at different dates and times of examination.

The CPU 70 sequentially changes the display region of the tomographic image 220 and the display region of the tomographic image 230 in accordance with the detected vector quantity that is produced by the drag operation on one of the tomographic image 220 and the tomographic image 230. Then, the CPU 70 outputs the tomographic images corresponding to the changed display regions in the given display areas on the monitor 75. The moving direction and the moving amount of the display region of the tomographic image 220 and the moving direction and the moving amount of the display region of the tomographic image 230 with respect to a given vector quantity are equal to each other. Accordingly, the tomographic image 220 and the tomographic image 230 are displayed moving substantially parallel to each other on the monitor 75 (FIG. 4 shows the state before the drag operation, and FIG. 5 shows the state after the drag operation).

The operation described above makes follow-up using the tomographic images easy because when the change of the display region of one of the tomographic images displayed on the monitor 75 is performed, the change of the display region of the other tomographic image is also performed in synchronization with the change of the display region of the one of the tomographic images.

In the description provided above, when a signal to instruct the change of the display region of one of the first and second tomographic images on the monitor 75 is outputted, the change of the display region of the other tomographic image is performed in synchronization with the change of the display region of the one of the tomographic images. However, the present invention is not limited thereto. It is essential only that the change of the display region be synchronized between the first and second tomographic images based on the operation signal outputted from the operation input unit. For example, a scroll bar may be provided to change the display regions of the tomographic images on the monitor 75 in synchronization.

On the other hand, when the apparatus is put into the non-synchronizing mode by using the synchronizing button 510 and the change of the display condition/the display region of one of the tomographic images is performed, the CPU 70 performs the change of the display condition/the display region only on the one of the tomographic images.

To be more specific, in the case of adjusting the zoom scale to a given zoom scale with the cursor 100 pointing the tomographic image 220, the CPU 70 adjusts the zoom scale of the tomographic image 220 to the given zoom scale. The zoom scale of the tomographic image 230 is not adjusted here. The brightness and the contrast of the tomographic images are adjusted in a similar manner.

Figure 6:
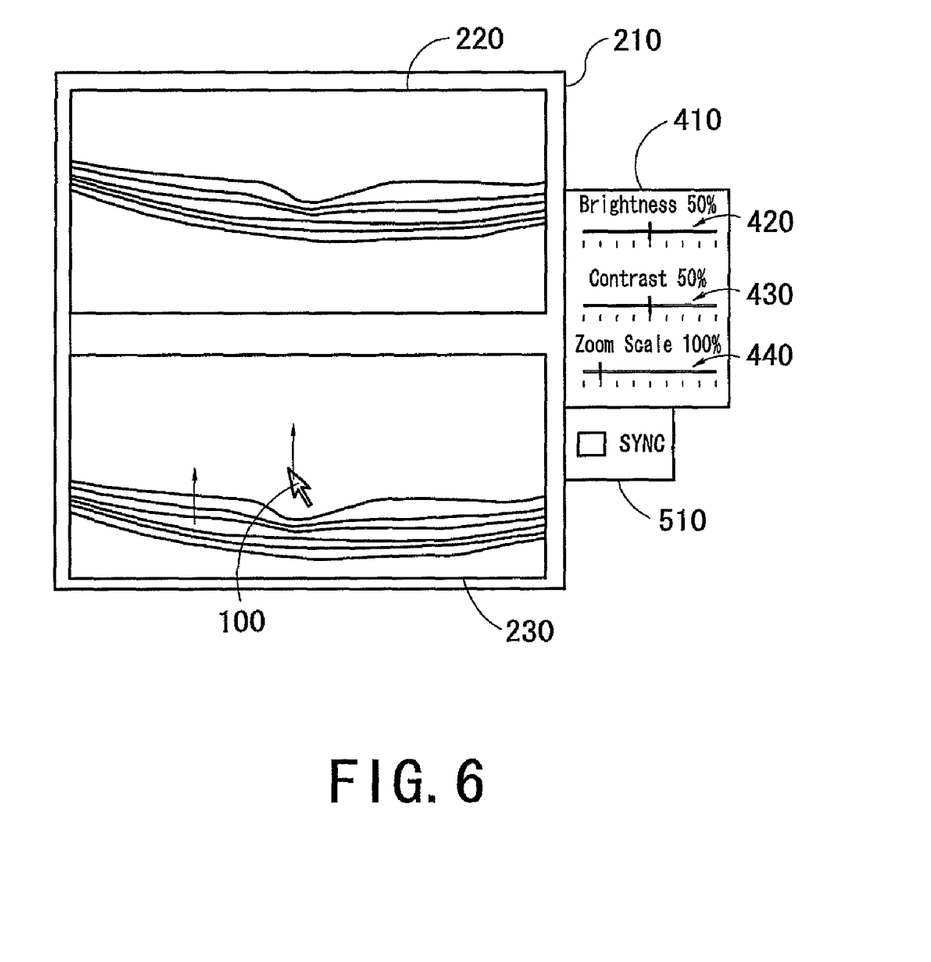
FIG. 6 shows an example of changing the display region of the tomographic image in a non-synchronizing mode.

When the drag operation is performed on the tomographic image 220, the CPU 70 sequentially changes the display region of the tomographic image 220 in accordance with a detected vector quantity. The CPU 70 outputs the tomographic image 220 corresponding to the changed display region in the given area on the monitor 75 (see FIG. 6). The display region of the tomographic image 230 is not changed here.

One example of the use of the non-synchronizing mode is for correcting before changing the display regions in the synchronizing mode a displacement of a display portion and a display position between the tomographic image 220 and the tomographic image 230 caused by a displacement of a photographing position during the obtainment of the tomographic images. In such a case, the examiner changes the display regions of the tomographic images by the drag operation in order that the same portion of the fundus may be displayed in substantially same display positions on the tomographic image 220 and the tomographic image 230.

The operation described above allows the examiner to easily compare the tomographic images in the same portion even if there is a displacement of the photographing position between the tomographic images when the display regions of the tomographic images are changed in the synchronizing mode. This operation is especially effective when the zoom scale of the tomographic image is large (the influence of the displacement of the photographing position is great).

The non-synchronizing mode may be used when the examiner intends to observe the tomographic images while paying attention to only one of the tomographic images or when the examiner focuses different positions on different tomographic images.

In the description provided above, the CPU 70 changes the display region of at least one of the tomographic image 220 and the tomographic image 230 based on the operation signal outputted from the mouse 76 and corrects the positional displacement between the tomographic image 220 and the tomographic image 230. However, the present invention is not limited thereto. It is essential only that the tomographic image 220 and the tomographic image 230 that are obtained by the ophthalmic photographing apparatus 10 be processed and the positional displacement between the tomographic image 220 and the tomographic image 230 be corrected.

For example, the CPU 70 may detect information on the positional displacement between the tomographic image 220 and the tomographic image 230 by image processing, change the display region of at least one of the tomographic image 220 and the tomographic image 230 based on the detected information on the positional displacement, and correct the positional displacement between the tomographic image 220 and the tomographic image 230.

In this case, for example, a positional displacement between two images is detected, and the images are subjected to image processing so as to correct the positional displacement. Alternatively a displacement of each of the images with respect to a reference position is detected, and the same portions of the images are corrected to the reference position. The time when the correction of the positional displacement is performed is not particularly limited. The correction may be performed every time each of the images is obtained or at the time when the images are displayed in a comparable manner.

The detection of the information on the positional displacement between the tomographic image 220 and the tomographic image 230 may be performed by various image processing methods (e.g., a method of using various correlation functions, a method of using the Fourier transform, a method of performing matching of characteristic points, a method of detecting a displacement between peak positions in luminance distributions in the depth direction).

In the above configuration, three or more images that are obtained at different dates and times of examination may be displayed on the monitor 75 in a comparable manner.

The tomographic images that are obtained at different dates and times of examination may be displayed on the monitor 75 in respect of two or more tomographic images that are obtained at different photographing positions (for example, tomographic images obtained when the measurement light is scanned in the right and left direction and in the up and down direction on the macular spot).

For example, at least a portion of a first tomographic image and at least a portion of a second tomographic image that are obtained at different dates and times of examination in respect of a first photographing position, and at least a portion of a third tomographic image and at least a portion of a fourth tomographic image that are obtained at different dates and times of examination in respect of a second photographing position are displayed on given display areas on the monitor 75 in a comparable manner. The first and third tomographic images are obtained at the same date and time of examination, and the second and fourth tomographic images are obtained at the same date and time of examination.

In the case of performing the change of the display condition/the display region on one of the four tomographic images in the synchronizing mode, if the one of the tomographic images is in respect of the first photographing position, the change of the display condition/the display region of the first tomographic image and the change of the display condition/the display region of the second tomographic image are performed in synchronization. If the one of the tomographic images is in respect of the second photographing position, the change of the display condition/the display region of the third tomographic image and the change of the display condition/the display region of the fourth tomographic image are performed in synchronization.

The present invention is applicable to a configuration such that two or more fundus front images (fundus front images that are obtained by an SLO or a fundus camera) that are obtained at different dates and times of examination on one examinee are displayed on a monitor in a comparable manner.

It is essential only that two or more images of an examinee's eye (images in a given portion of the eye) that are obtained at different dates and times of examination be displayed on a monitor in a comparable manner. For example, the present invention is applicable to a configuration in which tomographic images or front images of the anterior-segment of the eye are displayed on a monitor.

In the description provided above, the change of the display condition/the display region is performed on at least two images of the examinee's eye that are obtained at different dates and times of examination. However, the present invention is not limited thereto if at least two images of the examinee's eye that are obtained at the same photographing position can be compared. For example, the present invention is applicable to a configuration in which fundus images of right and left eyes that are obtained at the same date and time of examination by the ophthalmic photographing apparatus are previously obtained and at least a portion of the fundus image of the right eye and at least a portion of the fundus image of the left eye are displayed on given display areas on the monitor 75 in a comparable manner. The CPU 70 synchronizes the change of the display region between the fundus image of the right eye and the fundus image of the left eye when the change of the display region displayed on the monitor 75 is performed based on the operation signal outputted from the mouse 76.

At the time of displaying the fundus images (tomographic images) on the one follow-up screen in a comparable manner to be visually compared, a graph of layer thicknesses of the two tomographic images may be presented in order to allow for more efficient follow-up. The layer thickness graph and the previously selected tomographic images are displayed on the same follow-up screen in a comparable manner by the call-up operation of the follow-up screen described above.

Figure 7:
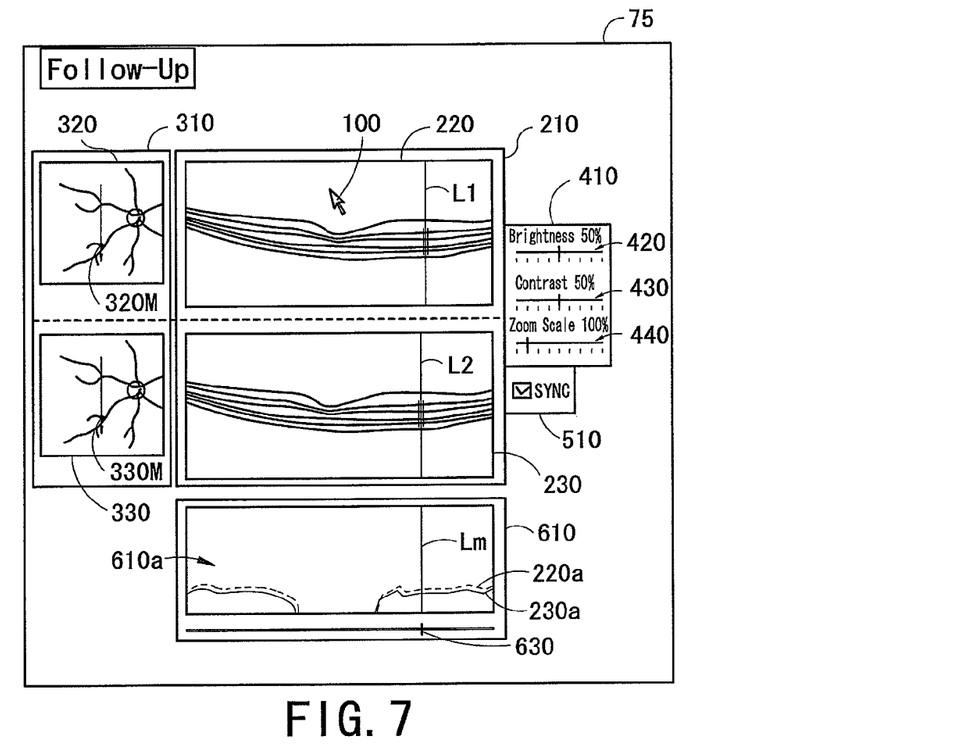
FIG. 7 shows an example of displaying a layer thickness graph for comparison between the two tomographic images that are obtained at different dates and times of examination.

A description of display control when displaying the layer thickness graph comparing the two tomographic images that are obtained at different dates and times of examination will be provided referring to FIG. 7. It should be noted that the constituent elements shown in FIG. 7 have the same function and configuration as the constituent elements shown in FIG. 2 having corresponding reference numerals unless specific descriptions are provided.

In FIG. 7, a layer thickness graph 610a showing distributions of layer thicknesses in a given portion of the fundus that are obtained based on the first tomographic image and the second tomographic image is displayed on a graph display region 610. The layer thickness graph 610a is prepared by measuring layer thicknesses in the depth direction and drawing a graph of distributions of the layer thicknesses at measurement positions with respect to the transverse direction. The layer thickness graph 610a is a graph of the layer thickness distributions for the tomographic images in which ILM (the inner limiting membrane) is set as a start layer and a boundary position between NFL (the nerve fiber layer) and GCL (the ganglion cell layer) is set as an end layer. In the layer thickness graph 610a, a graph 220a represented by dashed lines corresponds to the first tomographic image, and a graph 230a represented by solid lines corresponds to the second tomographic image.

When obtaining information on the layer thickness distributions of the tomographic images, the CPU 70 first detects boundary positions of the layers on the fundus by performing given image processing (e.g., edge detection) on the tomographic images stored in the memory 72. Then, the CPU 70 detects the thickness in a given portion of the fundus based on the detected boundary position information. In this case, the CPU 70 obtains the layer thickness distribution information in the given portion by obtaining the boundary position information corresponding to the previously set start layer and the boundary position information corresponding to the previously set end layer and obtaining a distance between the boundary positions.

It is essential only that the layer thickness information of the fundus to be graphed be information on a thickness of a layer of the fundus in the depth direction (a Z-direction). The layer thickness information of the fundus to be graphed may be the thickness of each layer or the sum of the thicknesses of a plurality of layers. For example, the layer thickness information may be information on the thickness of the nerve fiber layer, or information on the thickness from the surface of the retina to the choroid membrane. Instead of the layer thickness information of the tomographic images, information of the difference between the layer thickness distribution of the first tomographic image and the layer thickness distribution of the second tomographic image may be graphed.

On the layer thickness graph 610a, a line Lm extending in the depth direction (the layer thickness direction) is synthetically displayed. The CPU 70 displays the line Lm as a first indicator (marker) indicating a given measurement position on the layer thickness graph 610a.

The CPU 70 changes a display position of the line Lm based on the operation signal outputted from the mouse 76. To be more specific, a display position of a slider 630 below the layer thickness graph 610a is changed by operation of the mouse 76, and accordingly, the display position of the line Lm on the layer thickness graph 610a is changed with respect to the transverse direction.

The CPU 70 displays a line L1 and a line L2 as second indicators (markers) indicating measurement positions corresponding to the first indicator (the line Lm). To be more specific, the line L1 is synthetically displayed on the tomographic image 220, and the line L2 is synthetically displayed on the tomographic image 230. When the display position of the line Lm is changed, the CPU 70 displays the line L1 and the line L2 at the measurement positions corresponding to the line Lm of which the display position is changed.

On the front images in the front image display region 310, third indicators (markers) 320M and 330M indicating the measurement positions corresponding to the line Lm of the layer thickness graph 610a on the front images are displayed.

Figure 8:
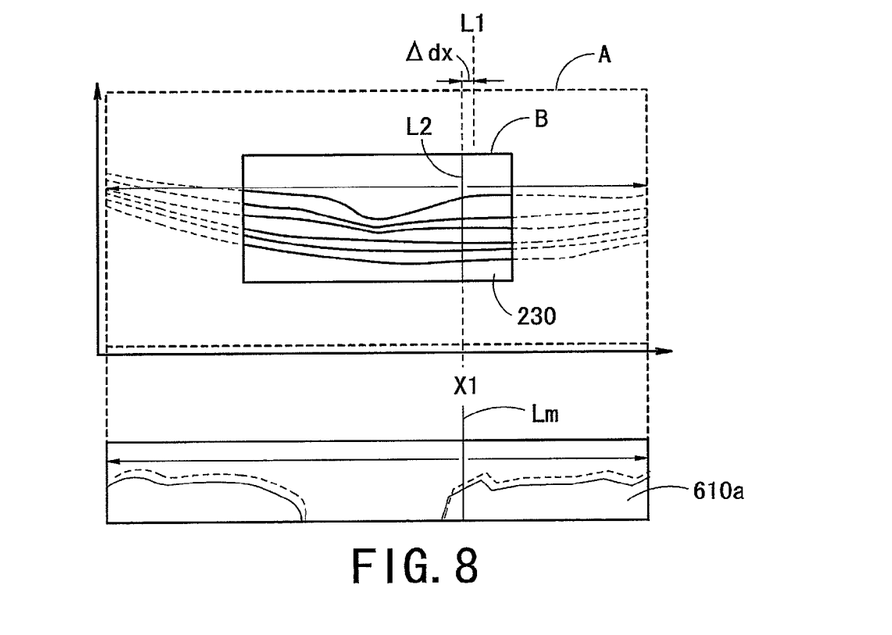
FIG. 8 is a schematic view for illustrating a correspondence relationship between a line on the layer thickness graph and a line on the tomographic image.

FIG. 8 is a view for illustrating a correspondence relationship between the line Lm on the layer thickness graph 610a and the line L2 on the tomographic image 230. The layer thickness graph 610a corresponds to the image data A and shows an overall layer thickness distribution of the first tomographic image (including also the second tomographic image) stored in the memory 72. The image data A and the layer thickness graph 610a have a correspondence relationship with respect to a coordinate position in the transverse direction.

The display region B in the second tomographic image is displayed as the tomographic image 230 on the monitor 75. The display position of the line Lm corresponds to the coordinate position X1 in the transverse direction in the image data A. The coordinate position X1 indicated by the line Lm corresponds to the display position of the line L2. Thus, the line L2 on the tomographic image 230 is displayed at the display position corresponding to the line Lm on the layer thickness graph 610a.

Figure 9:
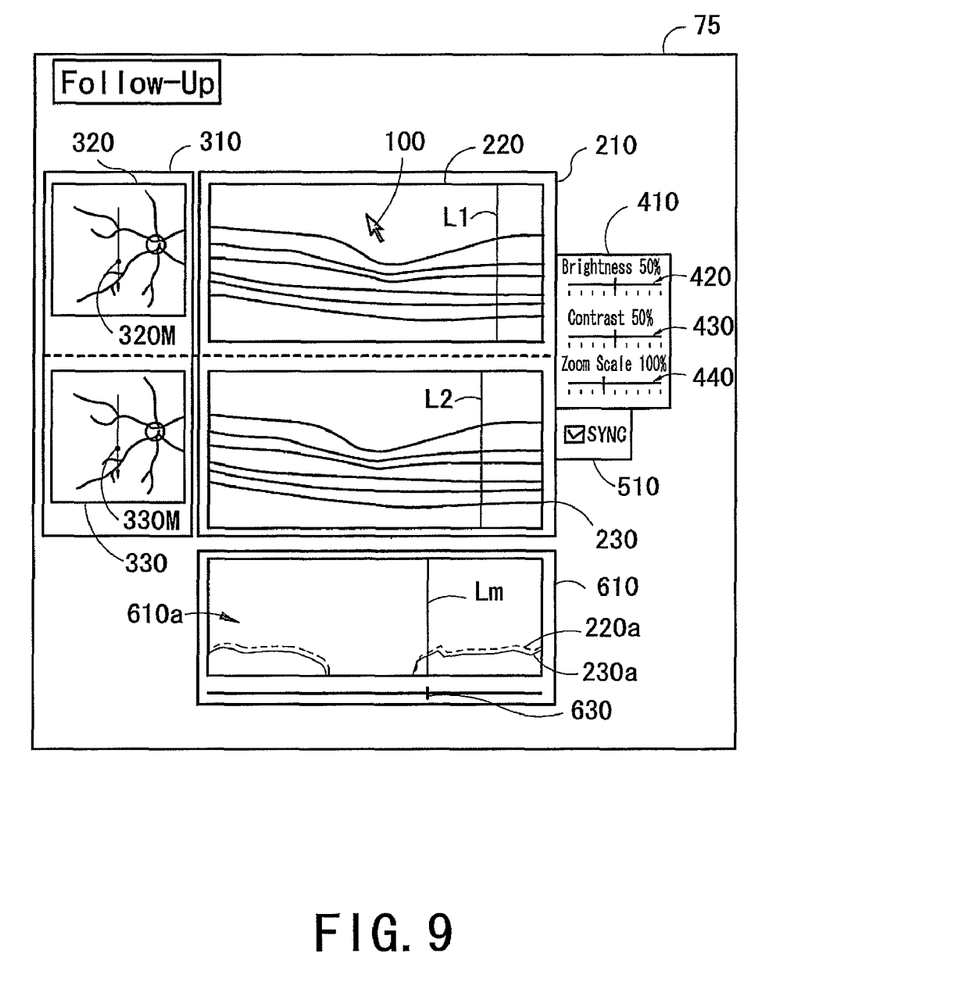
FIG. 9 is a view showing a display of the line on the thickness graph and the line on the tomographic image in a case where the zoom scale is 200%.

To be more specific, if the coordinate position X1 indicated by the line Lm is in the area corresponding to the display region B, the CPU 70 displays the line L2 at the display position corresponding to the coordinate position X1 in the display region B (FIG. 7 shows a case where the zoom scale is 100%, and FIG. 9 shows a case where the zoom scale is 200%). In addition, if the coordinate position X1 indicated by the line Lm is out of the area corresponding to the display region B, the CPU 70 displays the line L2 on the far-right position or the far-left position on the tomographic image 230 in accordance with the position of the coordinate position X1 with respect to the display region B.

When displaying the line L1, the CPU 70 detects a relative displacement of the photographing position between the first tomographic image and the second tomographic image based on the first fundus front image (corresponding to the first tomographic image) and the second fundus front image (corresponding to the second tomographic image) that are stored in the memory 72. The CPU 70 corrects the display position of the line L1 based on a detection result.

To be more specific, the CPU 70 compares the first front image and the second front image that are stored in the memory 72 and detects (calculates) a positional displacement direction and a positional displacement amount of the first front image with respect to the second front image by performing image processing. For the method of detecting the positional displacement between two images, various image processing methods may be used (e.g., a method of using various correlation functions, a method of using the Fourier transform, a method of using matching of characteristic points).

Next, the CPU 70 calculates a positional displacement direction and a positional displacement amount with respect to the transverse direction of the tomographic image (the scanning direction of the measurement light) based on the detected information on the positional displacement between the front images. The CPU 70 corrects the coordinate position X1 (to X1+Δdx) based on the positional displacement direction and amount Δdx and displays the line L1 at a display position corresponding to the corrected coordinate position (X1+Δdx).

The line L1 displayed on the tomographic image 220 is displayed in such a state that the displacement amount of the photographing position between the tomographic image 220 and the tomographic image 230 is offset relative to the display position corresponding to the line Lm on the layer thickness graph 610a. Accordingly, in a case where follow-up is performed by using two or more tomographic images that are obtained at different dates and times of examination, the line L1 and the line L2 are displayed on the substantially same portion of the fundus images even though there is a displacement of the photographing position between the tomographic images. This is especially effective when the zoom scale of the tomographic image is large (the influence of the displacement of the photographing position is large).

These operations allow the examiner to easily grasp the correspondence relationship between the first and second tomographic images displayed on the monitor 72 at the time of comparing the layer thicknesses of the first and second tomographic images by using the layer thickness graph 610a.

Displaying the line L1 and the line L2 as described above allows the examiner to easily grasp the displacement of the photographing position between the tomographic images. For example, in the synchronizing mode, the examiner can check the displacement of the photographing position with reference to the displacement of the display position between the line L1 and the line L2 when a given portion of the tomographic image 230 (e.g., a blood vessel portion) is displayed on the line L2.

The detection of the positional displacement and the offset of the display position of the line L2 may be performed with reference to the line L1 corresponding to the first tomographic image 220 contrary to the descriptions provided above.

The display of the tomographic images that are obtained at different dates and times of examination on the monitor 75 may be performed such that three-dimensional OCT images that are obtained at different dates and times of examination are previously obtained, and arbitrary tomographic images are obtained from three-dimensional data. The detection of the displacement of the photographing position may be performed by using fundus front images that are obtained by the front observation optical system 300 substantially simultaneously with the obtainment of the tomographic images, or by using an integrated image in the depth direction of a three-dimensional OCT image.

In the case of displaying the indicators of the measurement positions corresponding to the line Lm on the tomographic images, the indicators may be displayed at display positions corresponding to the graphed portion in the layer thickness graph 610a. For example, when the thickness distribution of the nerve fiber layer is displayed on the graph 610a, indicators (e.g., lines) may be displayed at display positions corresponding to the nerve fiber layer on the tomographic images on the monitor 72.

In the descriptions provided above, the linear indicators extending in the layer thickness direction are used as display patterns for making the measurement position on the layer thickness graph correspond to the measurement positions on the tomographic images. However, the present invention is not limited thereto, and various modifications may be performed. For example, the shape, size, color, and other factors of the indicators may be arbitrarily changed.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic observation apparatus for observing an image of an examinee's eye that is obtained by an ophthalmic photographing apparatus, the ophthalmic observation apparatus comprising:
   an input device arranged to output an operation signal given by an examiner;
   a monitor; and
   a display control unit arranged to
      display a first image and a second image of a same portion of the examinee's eye that are obtained at different dates and times of examination on the monitor in a comparable manner, wherein both of the first and second images comprise tomographic images that are obtained at a same photographing position, or both of the first and second images comprise front images that are obtained at a same photographing position; and when changing a display region of one of the first image and second image based on the operation signal outputted from the input device, synchronize the change of the display region between the first image and the second image in a manner that moving directions and moving amounts of the display regions of the images become equal to each other.

2. The ophthalmic observation apparatus according to claim 1, wherein when changing a display scale of the image of the examinee's eye based on the operation signal outputted from the input device, the display control unit synchronizes the change of the display scale between the first image and the second image.

3. The ophthalmic observation apparatus according to claim 2, wherein when the operation signal outputted from the input device comprises a signal to instruct the change of the display region or the display scale of one of the first image and the second image that are displayed on the monitor, the display control unit performs the change on the other image in synchronization with the change on the one of the images in the manner that the moving directions and the moving amounts of the display regions of the images become equal to each other.

4. The ophthalmic observation apparatus according to claim 2, further comprising a mode switching unit arranged to switch a mode of the displaying between a synchronizing mode of synchronizing the change of the display region or the display scale between the first image and the second image and a non-synchronizing mode of not synchronizing the change of the display region or the display scale between the first image and the second image, wherein when the operation signal outputted from the input device comprises a signal to instruct the change of the display region or the display scale of one of the first image and the second image that are displayed on the monitor, the display control unit performs the change only on the one of the images.

5. The ophthalmic observation apparatus according to claim 1, wherein:

the display control unit is arranged to display images of same portions of right and left eyes of the examinee that are obtained at a same date and time of examination on the monitor in a comparable manner, and when changing the display region of the image of the examinee's eye based on the operation signal outputted from the input device, synchronizes the change of the display region between the right eye image and the left eye image.

6. The ophthalmic observation apparatus according to claim 1, wherein:

the ophthalmic observation apparatus is an ophthalmic observation apparatus arranged to observe a tomographic image of a fundus of the examinee's eye that is obtained by an ophthalmic optical coherence tomography apparatus; and the display control unit is arranged to display a first tomographic image and a second tomographic image of a same portion of the fundus that are obtained at different dates and times of examination on the monitor in a comparable manner, based on the first tomographic image and the second tomographic image, display a layer thickness graph showing distributions of layer thicknesses in given portions of the fundus that are obtained based on the first tomographic image and the second tomographic image, and display on the layer thickness graph a first indicator indicating a measurement position on the layer thickness graph while changing a display position of the first indicator based on the operation signal outputted from the input device, and display a second indicator indicating a measurement position corresponding to the first indicator on the first tomographic image and the second tomographic image.

7. The ophthalmic observation apparatus according to claim 6, further comprising a positional displacement detection unit arranged to detect a relative displacement of a photographing position between the first tomographic image and the second tomographic image based on a first fundus front image corresponding to the first tomographic image and a second fundus front image corresponding to the second tomographic image, wherein the display control unit corrects a display position of the second indicator based on a detection result by the positional displacement detection unit.

8. The ophthalmic observation apparatus according to claim 6, wherein at least one of the first indicator and the second indicator comprises a linear indicator that extends in a direction of the thickness of the layer.

9. An ophthalmic observation program to be stored in a medium that is readable in a computer for observing an image of an examinee's eye that is obtained by an ophthalmic photographing apparatus, the ophthalmic observation program effecting an operation of the computer as a display control unit to:

display a first image and a second image of a same portion of the examinee's eye that are obtained at different dates and times of examination on the monitor in a comparable manner, wherein both of the first and second images comprise tomographic images that are obtained at a same photographing position, or both of the first and second images comprise front images that are obtained at a same photographing position; and when changing a display region of one of the first image and the second image based on an operation signal outputted from an input device, synchronize the change of the display region between the first image and the second image in a manner that moving directions and moving amounts of the display regions of the images become equal to each other.

* * * * *